United States Patent
Hassler et al.

(12) 
(10) Patent No.: US 9,788,959 B2
(45) Date of Patent: Oct. 17, 2017

(54) TRAPEZIOMETACARPAL JOINT IMPLANT AND ASSOCIATED METHODS

(71) Applicant: Tornier, Montbonnot-Saint-Martin (FR)

(72) Inventors: Michel Hassler, Saint Ismier (FR); Philippe Bellemere, Nantes (FR)

(73) Assignee: Tornier, Montbonnot-Saint-Martin (FR)

( * ) Notice: Subject to any disclaimer, the term of this patent is extended or adjusted under 35 U.S.C. 154(b) by 0 days.

(21) Appl. No.: 15/166,941

(22) Filed: May 27, 2016

(65) Prior Publication Data

US 2016/0346093 A1    Dec. 1, 2016

Related U.S. Application Data (62) Division of application No. 12/819,390, filed on Jun. 21, 2010, now Pat. No. 9,408,706.

(30) Foreign Application Priority Data

Jun. 19, 2009   (FR) ...................................... 09 54190

(51) Int. Cl.
*A61F 2/42*    (2006.01)
*A61F 2/30*    (2006.01)

(52) U.S. Cl.
CPC .......... *A61F 2/4261* (2013.01); *A61F 2/4241* (2013.01); *A61F 2002/302* (2013.01);
(Continued)

(58) Field of Classification Search
CPC ..................... A61F 2/4261; A61F 2002/30301
See application file for complete search history.

(56) References Cited

U.S. PATENT DOCUMENTS

| 4,759,766 A | * | 7/1988 | Buettner-Janz | ....... A61F 2/4425 |
| | | | | 623/17.15 |
| 4,936,860 A | | 6/1990 | Swanson | |

(Continued)

FOREIGN PATENT DOCUMENTS

| DE | 101 30 796 | 1/2003 |
| EP | 1 508 316 | 2/2005 |

(Continued)

OTHER PUBLICATIONS

European Search Report issued in European Patent Application No. 10166447, dated Oct. 25, 2010, in 4 pages.

(Continued)

*Primary Examiner* — Bruce E Snow
*Assistant Examiner* — Melissa Hoban
(74) *Attorney, Agent, or Firm* — Knobbe Martens Olson & Bear, LLP (57) ABSTRACT

A trapeziometacarpal joint implant includes a body defining a median plane, a metacarpal joint surface, and a trapezium joint surface. A first central region of the metacarpal joint surface is situated on an opposite side of the median plane from a second central region of the trapezium joint surface. The first and second central regions correspond to profiles of a first axial segment and a second axial segment, respectively. The first and second axial segments are one of a cylinder, a cone and a torus and are centered on a first axis and a second axis, respectively, where the first and second axes, as projected on the median plane, are substantially perpendicular to each other.

14 Claims, 5 Drawing Sheets

(52) U.S. Cl.
CPC ............... *A61F 2002/30153* (2013.01); *A61F 2002/30205* (2013.01); *A61F 2002/30224* (2013.01); *A61F 2002/30301* (2013.01); *A61F 2002/30616* (2013.01); *A61F 2002/30754* (2013.01); *A61F 2002/4258* (2013.01); *A61F 2230/0019* (2013.01); *A61F 2230/0065* (2013.01); *A61F 2230/0067* (2013.01); *A61F 2230/0069* (2013.01); *A61F 2230/0095* (2013.01); *A61F 2310/00173* (2013.01); *A61F 2310/00574* (2013.01)

(56) References Cited

U.S. PATENT DOCUMENTS

| | | |
|---|---|---|
| 5,314,486 A | 5/1994 | Zang et al. |
| 5,326,364 A | 7/1994 | Clift et al. |
| 5,425,777 A | 6/1995 | Sarkisian et al. |
| 5,549,690 A | 8/1996 | Hollister et al. |
| 5,683,466 A | 11/1997 | Vitale |
| 5,702,472 A | 12/1997 | Huebner |
| 6,017,366 A | 1/2000 | Berman |
| 6,436,146 B1 | 8/2002 | Hassler et al. |
| 8,012,217 B2 | 9/2011 | Strzepa et al. |
| 2006/0241758 A1 | 10/2006 | Peterman et al. |
| 2006/0241777 A1 | 10/2006 | Partin et al. |
| 2007/0123993 A1 | 5/2007 | Hassler et al. |
| 2008/0051912 A1 | 2/2008 | Hollawell |
| 2009/0254190 A1 | 10/2009 | Gannoe et al. |
| 2010/0057216 A1 | 3/2010 | Gannoe et al. |
| 2010/0249942 A1 | 9/2010 | Goswami et al. |

FOREIGN PATENT DOCUMENTS

| | | |
|---|---|---|
| EP | 1 637 095 | 3/2006 |
| EP | 2 263 614 | 1/2010 |
| FR | 2 465 470 | 3/1981 |
| FR | 2 709 948 | 3/1995 |
| FR | 2 957 780 | 9/2011 |
| WO | WO 97/42895 | 11/1997 |
| WO | WO 98/47449 | 10/1998 |
| WO | WO 2004/093767 | 11/2004 |
| WO | WO 2006/000890 | 1/2006 |

OTHER PUBLICATIONS

French Preliminary Search Report issued in French Patent Application No. 0954190, dated Feb. 23, 2010, in 6 pages.
French Search Report issued in French Patent Application No. 0954190, dated Apr. 13, 2011, in 2 pages.
French Search Report and Written Opinion issued in French Application No. 1152587, dated Oct. 24, 2011 in 5 pages.
French Search Report issued in French Patent Application No. 1256863, dated Mar. 28, 2013, in 2 pages.

* cited by examiner

TRAPEZIOMETACARPAL JOINT IMPLANT AND ASSOCIATED METHODS

INCORPORATION BY REFERENCE TO ANY PRIORITY APPLICATIONS

The present application is a divisional of U.S. patent application Ser. No. 12/819,390, filed on Jun. 21, 2010, which claims the benefit of French Patent Application No. FR0954190, filed on Jun. 19, 2009, and entitled "IMPLANT D'ARTICULATION TRAPÉZO-MÉTACARPIENNE," which is incorporated herein by reference in its entirety for all purposes.

BACKGROUND OF THE INVENTION

Trapeziometacarpal prostheses and implants are designed to restore the strength and mobility of the anatomical joint of the thumb, between its metacarpal and the trapezium, when the joint is damaged by a degenerative or inflammatory pathological process. Many trapeziometacarpal prostheses are stem prostheses in which the metacarpal prosthetic component is anchored at one end in the metacarpal by an elongate stem while the other end of the prosthetic component is mounted pivotably either in a prosthetic component attached to the trapezium or in a cavity hollowed out in the trapezium. The implantation of these total or partial prostheses requires considerable cutting of the bone substance of the trapeziometacarpal joint and restores a ball-and-socket type of mobility which, from the point of view of kinematics, does not correspond to the mobility of the anatomical joint. Moreover, in the event of poor implantation, there are real risks of wear, luxation, or even prosthesis fracture. Some trapeziometacarpal implants without stems have also been proposed, those implants being implanted into a cavity or cavities formed in the trapezium and/or metacarpal. Often times, because of the compressive stresses applied to the implant body by the surrounding ligaments of the joint, the implant body gradually engages deeper in the bones, reducing the space between the bones and, consequently, their relative mobility.

SUMMARY OF THE INVENTION

Some embodiments relate to a trapeziometacarpal implant that is permanently or semi-permanently implantable and provides mobility more similar to natural, anatomical mobility of the trapeziometacarpal joint. The trapeziometacarpal joint implant includes a body defining a metacarpal joint surface and a trapezium joint surface that are situated, at least in their central region, on either side of a median plane of the body. Each of the metacarpal and the trapezium joint surfaces correspond to a profile of an axial segment of a cylinder, a cone, or a torus, the axial segments of the cylinder, cone and/or torus being centered on respective axes which, as projected on the median plane, are substantially perpendicular to each other.

Some embodiments relate to a surgical method for fitting a trapeziometacarpal joint implant in which an articular area between the metacarpal and trapezium of a patient is accessed, the cortical bone surface of the trapezium is prepared so as to substantially match the trapezium joint surface defined by a body of an implant and, if need be, the cortical bone surface of the metacarpal is prepared so as to substantially match a metacarpal joint surface defined by the body of the implant, and the body of the implant is interposed between the trapezium and the metacarpal in such a way that an axis associated with the trapezium joint surface extends in either the antero-posterior or frontal plane of the patient, while an axis associated with the metacarpal joint surface extends in the other of the antero-posterior or front planes.

Some embodiments relate to interposing between the trapezium and the metacarpal a relatively thin body (e.g., as opposed to a body that is voluminous and spherical or ellipsoid) with opposite joint surfaces which are concave at least in one direction and against which the cortical bone surfaces of the trapezium and of the metacarpal come to bear so as to roll and slide thereon. In order to reproduce the anatomical behavior of the saddle-type trapeziometacarpal joint, the two joint surfaces correspond to profiles of axial segments of a cylinder, cone and/or torus, of which the central axes or, more generally, taking account that the central axis of an axial segment of a torus is curved, the projections of these central axes on the median plane of the implant, are substantially perpendicular to each other.

In some embodiments, the body of the implant simulates the anatomical saddle-type trapeziometacarpal joint with the two joint surfaces. From the point of view of kinematics, the two, orthogonal joint surfaces of the implant body permit pivoting mobility about the two aforementioned central axes, in the manner of a cardan joint, or universal joint, to which the trapeziometacarpal joint is similar from a mechanical point of view. Moreover, the curvature of the two joint surfaces stabilizes and aligns the body of the implant between the trapezium bone and the metacarpal bone, thus avoiding the need to provide means of fixation to the bone(s). Moreover, by maximizing an area of contact between the implant and the bones of the trapezium and metacarpal in the area of the two joint surfaces, the implant body is adapted to reduce the likelihood of being forced into the bones, thereby retaining mobility of the joint.

In some embodiments, the body of the implant is minimized in thickness, where a range of thicknesses are optionally offered to a surgeon during implantation depending on a degree of wear of the joint that is being treated. Generally, the natural contours of the trapezium and metacarpal cortical bone surfaces are well-matched for cooperating with the joint surfaces of the implant. In cases of substantial wear, however, minimizing thickness of the implant helps minimize an amount of bone cutting required to match the mutually facing cortical bone surfaces of the trapezium and of the metacarpal to the joint surfaces of the body of the implant. In turn, for some trapeziometacarpal joints that are not greatly damaged, resection of the metacarpal can be minimal or even unnecessary. Typically, the size of the implant is selected such that the implant body is stabilized by the stress provided by the capsular and ligament envelope around the joint between the trapezium and the metacarpal, without the implant body being overstressed. For example, in some embodiments, the implant body retains a certain degree of freedom of movement to help the implant adjust its position, or adapt, as a function of the stresses of the articular envelope associated with the various possible movements of the trapeziometacarpal joint.

Various embodiments relate to a trapeziometacarpal joint implant having a trapezium joint surface and a metacarpal joint surface opposite the trapezium joint surface. In some embodiments, one or both of the metacarpal and trapezium joint surfaces correspond to a profile of an axial segment of a cylinder, a cone, or a torus having a cross section that is curved, curved inward along its entire periphery, elliptic, and/or circular. In some embodiments, the cross section associated with the metacarpal and/or trapezium joint surface has, in the central region of the joint surface, a smaller curvature than a remainder of the cross section and, if desired, in the peripheral region of the joint surface, a greater curvature than a remainder of the cross section. The metacarpal and trapezium joint surfaces are separated from each other, in a direction perpendicular to a median plane of the implant, by a maximum thickness of the body of less than 5 mm, according to some embodiments. The trapezium joint surface optionally has a dimension, along its associated axis, greater than the dimension of the metacarpal joint surface along its associated axis. In some embodiments, the body is without any means of fixation to bone and the implant body is formed as a single, unitary component.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings. The intention, however, is not to limit the invention to the particular embodiments depicted. On the contrary, the invention is intended to cover all modifications, permutations, equivalents, and alternatives falling within the scope of the invention as defined by the appended claims.

DETAILED DESCRIPTION OF THE PREFERRED EMBODIMENT

Figure 1:
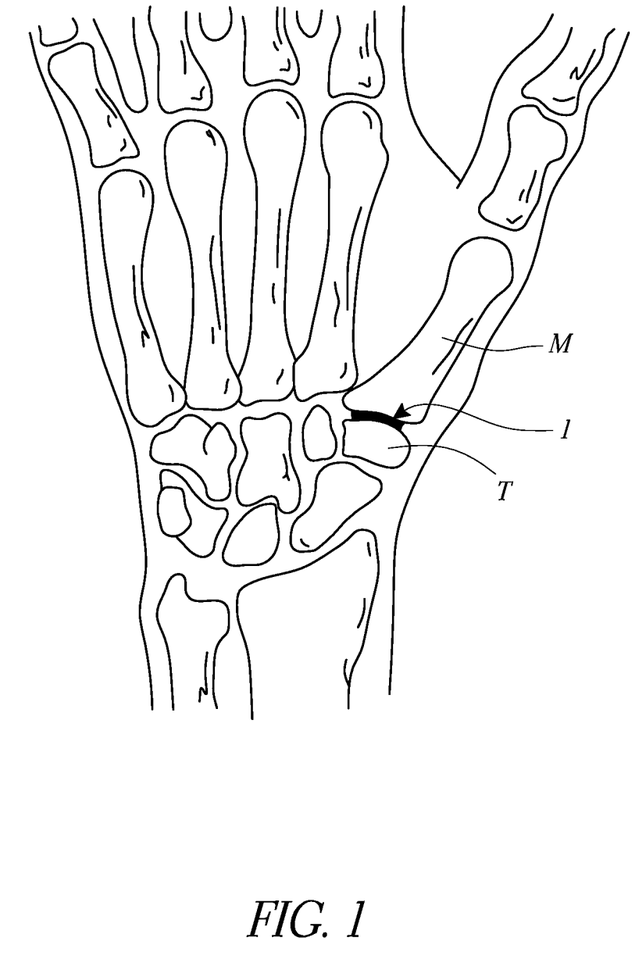
FIG. 1 is an elevation view showing an implant interposed between a trapezium and metacarpal of a human hand, according to some embodiments.
Figure 2:
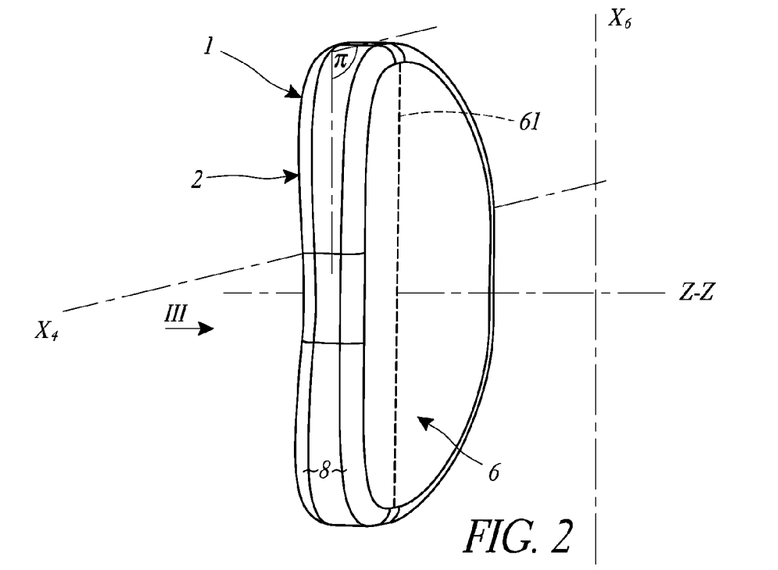
FIG. 2 is a perspective view of the implant of FIG. 1, according to some embodiments.
Figure 3:
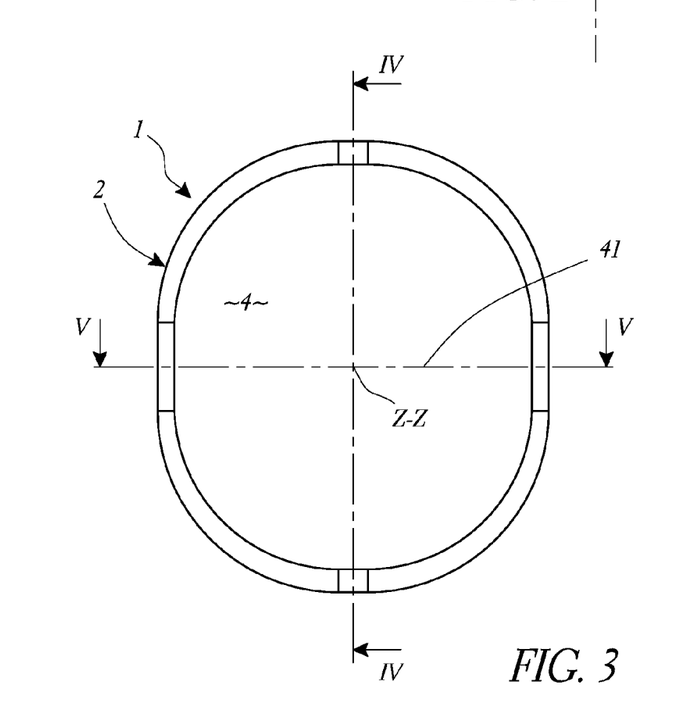
FIG. 3 is an elevation in the direction of the arrow III in FIG. 2, according to some embodiments.

As used herein, the terms "frontal," "antero-posterior," and similar terms are to be understood in their anatomical sense in relation to a patient whose hand is being operated upon. With that in mind, in FIGS. 1 to 5, a trapeziometacarpal implant 1 is shown which is designed to be implanted by interposition in a trapeziometacarpal joint between a trapezium T and a first metacarpal M of a human hand, as is shown by way of example in FIG. 1.

The implant 1 comprises a generally disk-shaped body 2 centered on a geometric axis Z-Z, also described as a transverse axis. The body 2 delimits a first main surface 4 and a second main surface 6, also referred to as metacarpal and trapezium joint surfaces, respectively, or primary bone contact surfaces, for example. In some embodiments, the first and second main surfaces 4 and 6 are positioned opposite each other on the axis Z-Z and separated from each other by the thickness of the body 2 along the axis Z-Z. The body 2 also includes a peripheral surface 8 that connects the first and second main surfaces 4 and 6. In some embodiments, the generatrices of the peripheral surface 8 are parallel to the axis Z-Z.

As shown, the transverse profile of the body 2 is generally rectangular. In particular, in a cross section that is transverse to the axis Z-Z, the body 2 has a rectangular outer contour with rounded corners, although a variety of shapes are contemplated, including square, circular, elliptical, and others, for example.

As shown, the implant 1 is formed as a single, unitary piece, consisting of the body 2 without extraneous components, such as a bone fixation component (e.g., a screw) for anchoring the body 2 in the metacarpal M or in the trapezium T. For example, in some embodiments, the body 2 is secured in position via interposition between metacarpal M and the trapezium T such that the body retains some freedom of movement to adapt its position to the stresses applied to it as a function of movements of the trapeziometacarpal joint.

In some embodiments, the body 2 is formed as a single piece of graphite covered with a layer of pyrolytic carbon, which provides good biocompatibility, high mechanical strength, and resists wearing of the metacarpal and the trapezium. Although graphite and pyrolytic carbon have been referenced, other materials are contemplated, including metals such as chromium cobalt alloys and plastics, such as polyethylene, PEEK, silicone, as well as ceramics and others.

Figure 4:
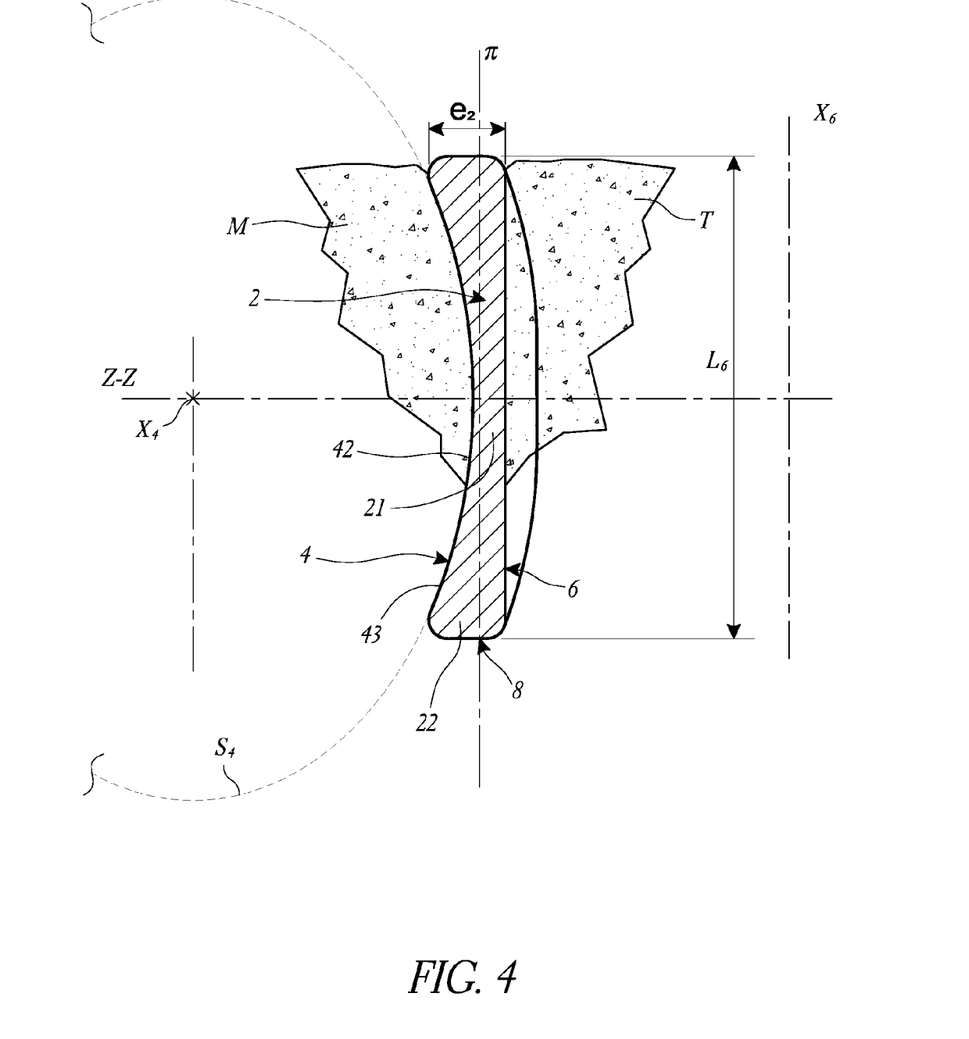
FIGS. 4 and 5 are sections along the lines IV-IV and V-V, respectively, from FIG. 3, also showing some of the bones of the hand after the implant of FIG. 1 has been positioned, according to some embodiments.

As shown in FIG. 4, the first main surface 4 is concave and corresponds geometrically to a profile of an axial segment of a cylinder portion which is centered on a first axis $X_4$ and defines a first cross section $S_4$ that is substantially elliptic. In some embodiments, the first cross section $S_4$ is constant along the first axis $X_4$ and corresponds to the directrix of the first main surface 4. As shown, the first axis $X_4$ extends perpendicular to the axis Z-Z, the axes $X_4$ and Z-Z intersecting with one another (for reference, the first axis $X_4$ extends in and out of the page as depicted in FIG. 4).

Figure 5:
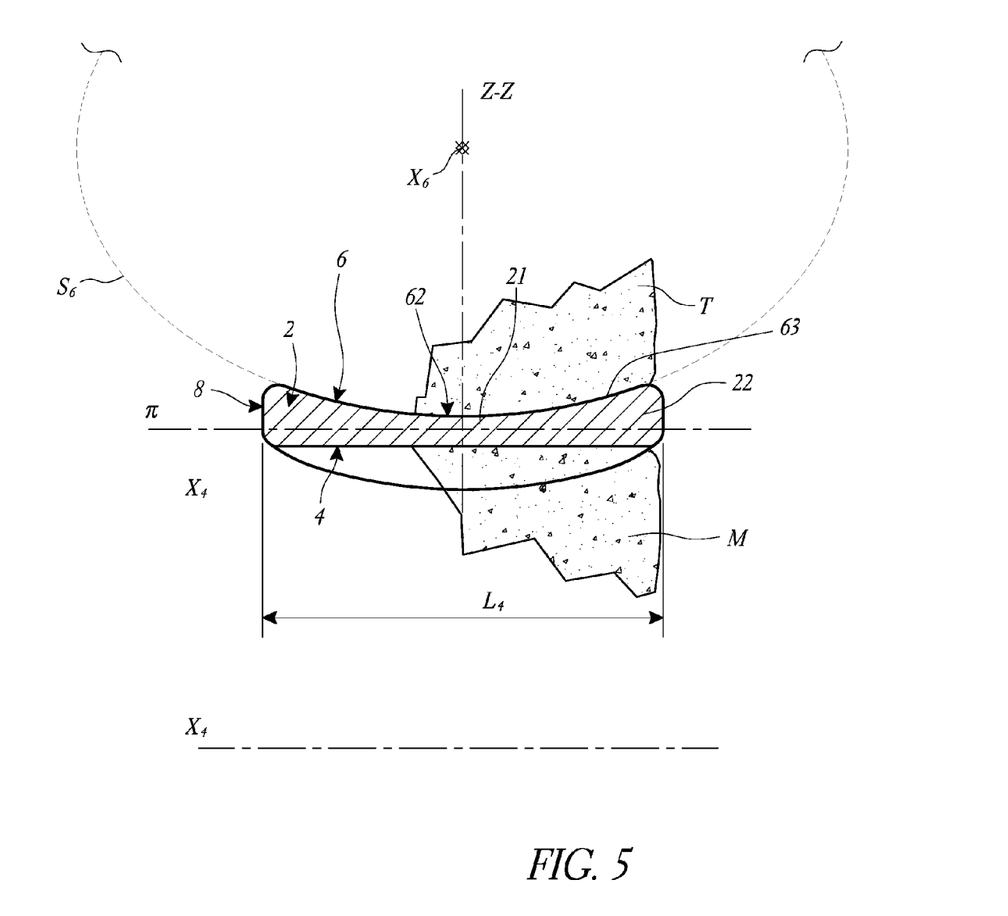

As shown in FIG. 5, the second main surface 6 is also concave and corresponds to a cylinder portion whose second cross section $S_6$ is substantially elliptic and which is centered on a second axis $X_6$ perpendicular to and intersecting the axis Z-Z (for reference, the axis $X_5$ extends in and out of the page as depicted in FIG. 5).

Thus, as shown, the axes $X_4$ and $X_6$ extend perpendicular to each other and do not intersect. Base lines 41 (FIG. 2) and 61 (FIG. 3) belong respectively to the first and second main surfaces 4 and 6. Each of the base lines 41 and 61 extend parallel to the axes $X_4$ and $X_6$ and are perpendicular to each other. The base lines 41 and 61 are separated, on the axis Z-Z, by a central part 21 of the body 2. In different terms, in a median plane π of the body 2, which is perpendicular to the axis Z-Z and on either side of which the first and second main surfaces 4 and 6 are situated, the respective projections of the axes $X_4$ and $X_6$ are perpendicular and secant.

In some embodiments, in cross section through the axis Z-Z, the body 2 has a variable thickness, the thickness being at its minimum in the central part 21 of the body and gradually increasing in the direction away from the central part 21 toward a peripheral part 22 of the body 2, as shown in FIGS. 4 and 5.

The following method of fitting the implant in place between the metacarpal M and the trapezium T is accordance with some embodiments and is provided by way of example. Thus, in some embodiments, a first operating step includes a surgeon accessing the articular area between the metacarpal M and the trapezium T via a posterior or anterolateral approach. To access the interosseous space between the metacarpal and the trapezium, the articular capsule and the ligaments surrounding the articular area are either preserved, by being retracted, or are partially incised, it being understood that the capsule and its ligaments will then be reconstructed at the end of intervention.

In some embodiments, in a second operating step, the surgeon moves the metacarpal M and the trapezium T apart from each other in order to widen the interosseous space, in particular by applying a tensile force in the longitudinal direction of the metacarpal. The surgeon is then better able to prepare the bone surfaces delimited by the metacarpal M and the trapezium T, in such a way as to shape these surfaces so that they match the first and second main surfaces 4 and 6 of the body 2 of the implant 1.

In practice, it will be noted that the mutually facing ends of the metacarpal M and of the trapezium T have respective surface geometries that are close to surfaces matching the first and second main surfaces 4 and 6. This is because these bone ends, in their anatomical state, have saddle shapes, which fit orthogonally one into the other. Thus, the cuts made in the bone on the mutually facing ends of the metacarpal M and the trapezium T for adapting the surface of the bones M and T to the surfaces 4 and 6 of the body 2 can be minimal, according to some embodiments. In particular, the cuts are often minimal or even unnecessary on the metacarpal M, whereas more substantial cuts may have to be made on the trapezium T. In some embodiments, preparation of the ends of the metacarpal M and/or of the trapezium T does not require any deep cutting into the bones, as cutting remains confined to the cortical bone layer.

In some embodiments, in a third operating step, the tension applied to the trapeziometacarpal joint in the longitudinal direction of the metacarpal M is maintained. The surgeon positions the implant 1 in the interosseous space separating the metacarpal M and the trapezium T by interposing the body 2 between the two bones M and T in such a way that the first main surface 4 is directed toward the metacarpal M, with the first axis $X_4$ extending in a frontal plane, while the second main surface 6 is directed toward the trapezium T, with the second axis $X_6$ extending in an antero-posterior plane.

In a variant not shown, the implant 1 is fitted in place, between the metacarpal M and the trapezium T, in a configuration tilted by 90 degrees about the axis Z-Z. The ends of the metacarpal M and of the trapezium T are prepared in advance of fitting the implant 1, according to some embodiments. Regardless, the body 2 is optionally implanted in such a way that the first and second main surfaces 4 and 6 adapt better to the ends of the metacarpal M and trapezium T of the patient being operated on, depending on the initial state of these bone ends, and/or to minimize a depth to which the bone ends are cut during preparation.

Once the implant 1 has been positioned, or interposed, between the metacarpal M and the trapezium T, the axial tension applied to the trapeziometacarpal joint is released, such that the articular capsule and the ligaments surrounding the trapeziometacarpal joint move the metacarpal M and the trapezium T toward each other. In some embodiments, the body 2 of the implant 1 and/or the metacarpal M and trapezium T are adapted such that the implant 1 is held movably between the metacarpal M and the trapezium T, under the stress provided by the capsule and the ligaments. In other words, the capsule and the ligaments provide a stress whose resultant force, or a substantial component thereof, is substantially aligned with the axis Z-Z. The surgeon then closes the soft tissues around the trapeziometacarpal joint, if appropriate by reconstruction, or by ligamentoplasty, for example.

The trapeziometacarpal joint thus fitted with the implant 1 exhibits a kinematic behavior similar to, or even nearly identical to the natural anatomical behavior of the trapeziometacarpal joint. For example, the implant 1 is configured such that the metacarpal M articulates against the first main surface 4 by tilting about the first axis $X_4$ whereas the trapezium T concurrently articulates against the second main surface 6 by tilting about the second axis $X_6$. By virtue of the implant 1, the metacarpal M and the trapezium T are articulated with respect to each other in the manner of a cardan joint, or universal joint, about the two perpendicular axes $X_4$ and $X_6$. These cardan joint kinematics efficiently reproduce the anatomical, saddle-type joint typically present between the metacarpal M and the trapezium T. Moreover, according to some embodiments, the first and second main surfaces 4 and 6 rest against the respective cortical bone layers of the metacarpal M and of the trapezium T, which helps prevent the body 2 from being forced into, or further penetrating one and/or the other of the metacarpal and trapezium bones M and T. By reducing the risk of this sinking effect of the implant 1 into bone, the mobility afforded by the implant 1 is longer lasting, and potentially lifelong in duration.

In some embodiments, in order to promote the rolling and sliding movements of the metacarpal M and of the trapezium T against the respective central parts 42 of the first and second main surfaces 4 and 6, the first and second, elliptic cross sections $S_4$ and $S_6$ of the first and second main surfaces 4 and 6 have, in the central regions 42 and 62, a smaller curvature than a remainder of the cross section. In other words, the central regions 42 and 62 of the first and second main surfaces 4 and 6 are more flattened relative to the surrounding portions of the implant 1, such as the peripheral regions 43 and 63, the central regions 42 and 62 being less curved than the rest of these surfaces. In some embodiments, the difference in curvature of the first and second cross sections $S_4$ and $S_6$ of the first and second main surfaces 4 and 6 between the central regions 42 and 62 and the peripheral regions 43 and 63 of the implant is relatively minor, while still having the desired effect.

In some embodiments, when in use, the body 2 is stabilized between the metacarpal M and the trapezium T on account of the elliptic curvature of the respective first and second cross sections $S_4$ and $S_6$ of the first and second main surfaces 4 and 6. In order to reinforce this stability, the first and second cross sections $S_4$ and $S_6$ of the respective peripheral regions 43 and 63 of the first and second main surfaces 4 and 6 have a greater curvature than the rest of the cross section. By exaggerating the curvature of the surfaces 4 and 6 in the area of their periphery, the surface cooperation of the body 2 with the metacarpal M and the trapezium T self-stabilizes the implant 1. Furthermore, the peripheral regions 43 and 63 of the surfaces 4 and 6 can thus compensate for the peripheral wear, associated with arthrosis, of the mutually facing bone ends of the metacarpal M and trapezium T.

As shown, the body 2 is an implant of interposition. Thus, the thickness of the implant 1 along the axis Z-Z is limited, in the sense that the presence of the body 2 is adapted to avoid overstressing the trapeziometacarpal joint. Thus, in some embodiments, the maximum thickness $e_2$ of the body 2 (e.g., the thickness between the peripheral regions 43 and 63 of the first and second main surfaces 4 and 6), is less than 5 mm, and preferably equal to about 1 mm, although a variety of dimensions are contemplated. Similarly, in order to adapt optimally to the interosseous space between the metacarpal M and the trapezium T, the second main surface 6 has a dimension $L_6$, along its second axis $X_6$, that is greater than a dimension $L_4$ of the first main surface 4 along the first axis $X_4$.

Figure 6:
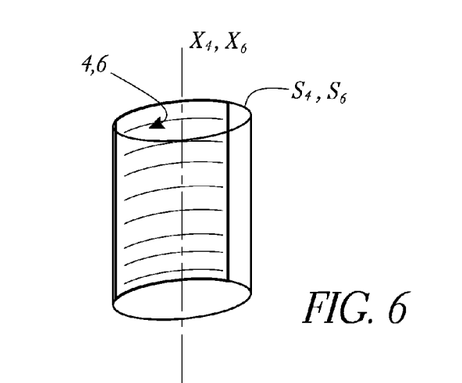
FIG. 6 is a diagram illustrating a design geometry of joint surfaces of the implant of FIG. 1, according to some embodiments.

The geometry of the first and second main surfaces 4 and 6 are optionally constructed with different shapes than described above. FIG. 6 is a diagram for visualizing a geometry of the first and second main surfaces 4 and 6 as shown in FIGS. 1 to 5. As shown in FIG. 6, the first and second main surfaces 4 and 6 correspond to profiles of axial segments, or portions, of cylinders defining the first and second axes $X_4$ and $X_6$, respectively. As shown, the axial segments have elliptical bases. In particular, the first and second cross sections $S_4$ and $S_6$ of the first and second main surfaces 4 and 6 have elliptic shapes centered on the first axis $X_4$ and second axis $X_6$, respectively. Thus, the geometric definition referenced above for the first and second main surfaces 4 and 6 is again shown here in a more schematic form.

Figure 7:
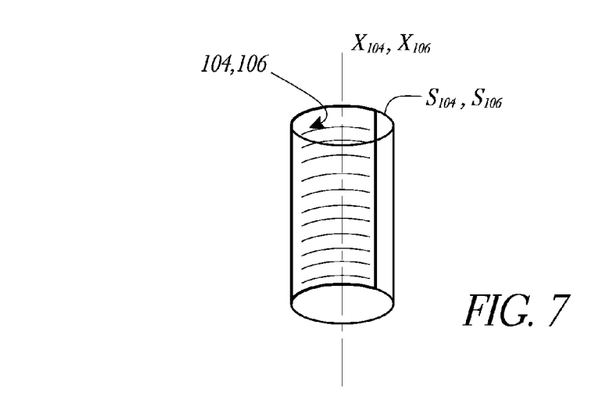
FIGS. 7 to 9 are diagrams illustrating other design geometries of joint surfaces of other implants, according to some embodiments.
Figure 8:
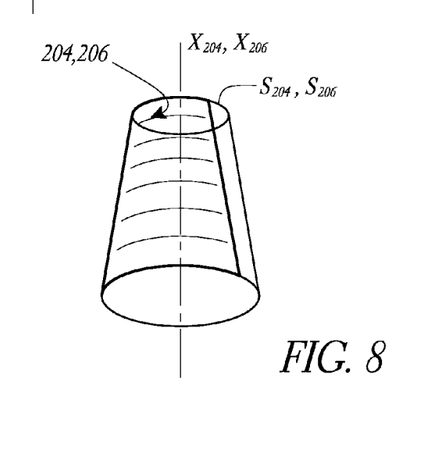
Figure 9:
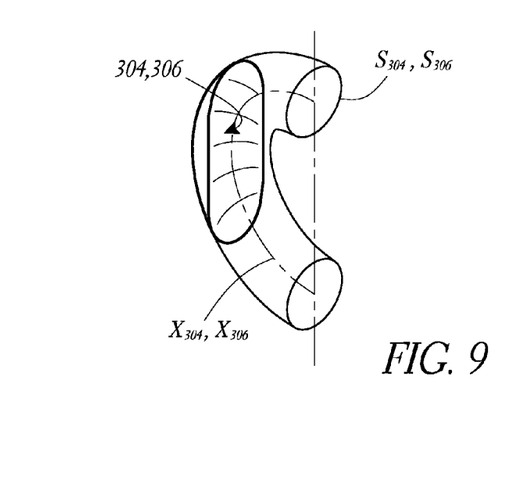

FIGS. 7, 8 and 9 are diagrams similar to the one in FIG. 6 showing geometric variants of the first and second main surfaces 4 and 6 of the implant 1. In FIG. 7, first and second main surfaces 104 and 106, also described as metacarpal and trapezium joint surfaces, respectively, are represented, each of which correspond to a profile of an axial segment of a cylinder that is centered on first and second axes $X_{104}$ and $X_{106}$, respectively, and of which the first and second cross sections $S_{104}$ and $S_{106}$, respectively, are circular and centered on the aforementioned axes. In other words, in some embodiments, the first and second main surfaces 4 and 6 and the first and second main surfaces 104 and 106 differ only in terms of the geometric shape of their cross section, namely elliptical for the first and second main surfaces 4 and 6 and circular for the first and second main surfaces 104 and 106.

Similarly, in FIG. 8, first and second main surfaces 204 and 206, respectively, are represented, each of which corresponds to a profile of an axial segment of a cone that is centered on first and second axes $X_{204}$ and $X_{206}$, respectively, and of which the first and second cross sections $S_{204}$ and $S_{206}$, respectively, are circular. In yet another variant not depicted, the aforementioned first and second cross sections $S_{204}$ and $S_{206}$ are elliptic, rather than circular.

Likewise, in FIG. 9, first and second main surfaces 304 and 306, respectively, are represented, each of which corresponds to a profile of an axial segment of a torus that is associated with circular, central, first and second axes $X_{304}$ and $X_{306}$, respectively, and of which the first and second cross sections $S_{304}$ and $S_{306}$, respectively, that is to say the cross section in a plane perpendicular to the applicable axis, is circular and centered on the axes $X_{304}$ and $X_{306}$, respectively. In other variants not depicted, the first and second cross sections $S_{304}$ and $S_{306}$ of the aforementioned torus is made elliptical. Similarly, and once again in a variant not depicted, the circular cross section or the elliptical cross section of the torus, instead of being constant along the first and second axes $X_{304}$ and $X_{306}$, respectively, optionally increases or decreases along the first and second axes $X_{304}$ and $X_{306}$.

In still other embodiments, the curved geometry of the first and second cross sections $S_{104}$, $S_{106}$, $S_{204}$, $S_{206}$, $S_{304}$ and $S_{306}$ are continuously circular or elliptic or, by contrast, have substantial variations of curvature along their peripheries, for example. In particular, as has been mentioned above for the elliptic geometry of the first and second cross sections $S_4$ and $S_6$, the circular or elliptical geometry of the first and second cross sections $S_{104}$, $S_{106}$, $S_{204}$, $S_{206}$, $S_{304}$ and/or $S_{306}$ optionally have smaller curvatures in the central regions of the corresponding first and second main surfaces 104, 106, 204, 206, 304, and 306 and/or have a greater curvature in the peripheral regions of the first and second main surfaces 104, 106, 204, 206, 304, and 306 in relation to a remainder of the cross sections.

FIGS. 6 to 9 thus illustrate various design geometries of the metacarpal and trapezium joint surfaces, or first and second main surfaces of the implant 1, according to some various embodiments. Depending upon the application, the various design geometries provide desirable articular mobility simulating that of the natural trapeziometacarpal joint, once the body 2 is implanted, given that the two opposite first and second main surfaces 4 and 6, 104 and 106, 204 and 206, 304 and 306 of the implant 1 are arranged orthogonal to each other. In other words, the opposite first and second main surfaces 4 and 6, 104 and 106, 204 and 206, 304 and 306 of the implant 1 are arranged in such a way that their central, first and second axes $X_4$ and $X_6$, $X_{104}$ and $X_{106}$, $X_{204}$ and $X_{206}$, $X_{304}$ and $X_{306}$ extend substantially perpendicular to one other. In embodiments with surfaces having corresponding curved axes, such as the curved, first and second axes $X_{304}$ and $X_{306}$, the feature of perpendicularity between the particular set of opposing first and second main surfaces is exhibited via projection of the axes in the median plane π of the body 2 of the implant 1, where the respective central regions of the first and second main surfaces 304 and 306 are arranged on either side of the plane π (as is also the case with the projections on the plane π of the rectilinear, first and second axes $X_4$ and $X_6$, $X_{104}$ and $X_{106}$, $X_{204}$ and $X_{206}$, which are also perpendicular to each other).

Various modifications and additions can be made to the exemplary embodiments discussed without departing from the scope of the present invention. For example, although various embodiments have been described with similar, angularly offset shapes for the various first and second main surfaces, it is also contemplated that the design geometry of the first main surface is the same as, with strictly identical or different dimensioning, or different than, the design geometry chosen for the second main surface of the implant. Additionally, while the embodiments described above refer to particular features, the scope of this invention also includes embodiments having different combinations of features and embodiments that do not include all of the above described features.

What is claimed is:

1. A method of implant interposing for a trapeziometacarpal joint, the method comprising:
    providing a trapeziometacarpal joint implant including a body defining:
        a median plane,
        a metacarpal joint surface having a first central region, and
        a trapezium joint surface having a second central region, the first central region being situated on an opposite side of the median plane relative to the second central region, wherein the first central region and the second central regions correspond to profiles of a first axial segment and a second axial segment, respectively, the first and second axial segments being each one of a cylinder, a cone and a torus and being centered on a first axis and a second axis, respectively, the first and second axes, as projected on the median plane, being substantially perpendicular to each other;

accessing an articular area between a metacarpal and a trapezium of a patient; and interposing the trapeziometacarpal joint implant between the metacarpal and the trapezium in the articular area such that the metacarpal joint surface comes into direct contact and articulates with the metacarpal and the trapezium joint surface comes into direct contact and articulates with the trapezium.

2. The method of claim 1, wherein upon interposing the trapeziometacarpal joint implant between the metacarpal and the trapezium in the articular area, a tensile force is applied in a longitudinal direction of the metacarpal, then the trapeziometacarpal joint implant is positioned in the articular area while maintaining the tensile force, and then the tensile force is released to secure the trapeziometacarpal joint implant between the metacarpal and the trapezium.

3. The method of claim 1, wherein upon interposing the trapeziometacarpal joint implant between the metacarpal and the trapezium in the articular area, the body of the trapeziometacarpal joint implant separates the metacarpal and the trapezium by a thickness of less than 5 mm.

4. The method of claim 1, wherein the trapeziometacarpal joint implant is interposed between the metacarpal and the trapezium in the articular area such that the metacarpal is free to articulate against the metacarpal joint surface by tilting about the first axis and the trapezium is free to concurrently articulate against the trapezium joint surface by tilting about the second axis.

5. The method of claim 1,
wherein the articular area is defined by a bone cortical layer of the metacarpal and a bone cortical layer of the trapezium,
wherein the bone cortical layers of the metacarpal and of the trapezium are not completely removed before interposing the trapeziometacarpal joint implant between the metacarpal and the trapezium in the articular area,
and wherein upon interposing the trapeziometacarpal joint implant between the metacarpal and the trapezium in the articular area, the metacarpal joint surface comes into direct contact and articulates with the bone cortical layer of the metacarpal and the trapezium joint surface comes into direct contact and articulates with the bone cortical layer of the trapezium.

6. The method of claim 5, wherein before interposing the trapeziometacarpal joint implant between the metacarpal and the trapezium in the articular area, the bone cortical layer of the metacarpal is not reshaped.

7. The method of claim 5, wherein before interposing the trapeziometacarpal joint implant between the metacarpal and the trapezium in the articular area, the bone cortical layer of the metacarpal is reshaped so as to match the metacarpal joint surface.

8. The method of claim 5, wherein before interposing the trapeziometacarpal joint implant between the metacarpal and the trapezium in the articular area, the bone cortical layer of the trapezium is reshaped so as to match the trapezium joint surface.

9. The method of claim 1, wherein the trapeziometacarpal joint implant is interposed between the metacarpal and the trapezium in the articular area such that the first central region of the metacarpal joint surface comes into direct contact and articulates with the metacarpal and the second central region of the trapezium joint surface comes into direct contact and articulates with the trapezium.

10. The method of claim 1, wherein upon interposing the trapeziometacarpal joint implant between the metacarpal and the trapezium in the articular area, the body of the trapeziometacarpal joint implant is oriented in the articular cavity such that the first axis extends in a frontal plane of the patient and the second axis extends in an anteroposterior plane of the patient.

11. The method of claim 1, wherein upon interposing the trapeziometacarpal joint implant between the metacarpal and the trapezium in the articular area, the body of the trapeziometacarpal joint implant is oriented in the articular cavity such that the first axis extends in an anteroposterior plane of the patient and the second axis extends in a frontal plane of the patient.

12. The method of claim 1, wherein the articular area is accessed via a posterior approach.

13. The method of claim 1, wherein the articular area is accessed via an antero-lateral approach.

14. The method of claim 1, wherein after interposing the trapeziometacarpal joint implant between the metacarpal and the trapezium in the articular area, the body of the trapeziometacarpal joint implant is not anchored in the metacarpal and the trapezium so as to retain freedom of movement in use.

* * * * *